(12) United States Patent
Aberdam et al.

(10) Patent No.: US 7,186,558 B2
(45) Date of Patent: Mar. 6, 2007

(54) KERATINOCYTES OBTAINED FROM EMBRYONIC STEM CELLS OF MAMMALS

(75) Inventors: Daniel Aberdam, Nice (FR); Christelle Coraux, Nice (FR)

(73) Assignee: INSERM, Paris (FR)

( * ) Notice: Subject to any disclaimer, the term of this patent is extended or adjusted under 35 U.S.C. 154(b) by 50 days.

(21) Appl. No.: 10/478,830

(22) PCT Filed: May 30, 2002

(86) PCT No.: PCT/EP02/06030

§ 371 (c)(1),
(2), (4) Date: May 13, 2004

(87) PCT Pub. No.: WO02/097068

PCT Pub. Date: Dec. 5, 2002

(65) Prior Publication Data

US 2004/0248292 A1 Dec. 9, 2004

(30) Foreign Application Priority Data

May 31, 2001 (FR) .................................. 01 07167

(51) Int. Cl.
*C12N 5/00* (2006.01)
(52) U.S. Cl. ...................... 435/379; 435/366; 435/371
(58) Field of Classification Search ................ 435/366, 435/371, 377
See application file for complete search history.

(56) References Cited

U.S. PATENT DOCUMENTS

2002/0019046 A1 * 2/2002 Carpenter et al. .......... 435/368
2002/0146678 A1 * 10/2002 Benvenisty .................... 435/4

FOREIGN PATENT DOCUMENTS

WO  WO 81/01416  5/1981

OTHER PUBLICATIONS

Bradley et al. "Formation of Germ-Line Chimaeras from Embryo-Derived Teratocarcinoma Cell Lines". *Nature.* May 1984, vol. 309, pp. 255-256.
Nagy et al. "Embryonic Stem Cells Alone are Able to Support Fetal Development in the Mouse". *Development.* 1990, vol. 110, pp. 815-821.
Doetschman et al. "The In Vitro Development of Blastocyst-Derived Embryonic Stem Cell Lines: Formation of Visceral Yolk Sac, Blood Islands and Myocardium". *J. Embryol. exp. Morph.* 1985, pp. 27-45.
Wobus et al. "Specific Effects of Nerve Growth Factor on the Differentiation Pattern of Mouse Embryonic Stem Cell In Vitro". *Biomed. Biochem. Acta.* 1988, vol. 47, No. 12, pp. 965-973.
Robins et al. "Mouse Embryonic Stem Cells Express the Cardiac Myosin Heavy Chain Genes during Development in Vitro". *The Journal of Biological Chemistry.* Jul. 15, 1990, vol. 265, No. 20, pp. 11905-11909.

Schmitt et al. "Hematopoietic Development of Embryonic Stem Cells in Vitro: Cutokine and Receptor Gene Expression". *Genes & Development.* 1991, vol. 5, pp. 728-740.
Williams et al. "Myeloid Leukaemia Inhibitory Factor Maintains the Developmental Potential of Embryonic Stem Cells". *Nature.* Dec. 1988, vol. 336, pp. 684-687.
Smith et al. "Inhibition of Pluripotential Embryonic Stem Cell Differentation by Purified Polypeptides". *Nature.* Dec. 15, 1988, vol. 336, pp. 688-690.
Gearing et al. "Production of Leukemia Inhibitory Factor in *Escherichia coli* by a Novel Procedure and its use in Maintaining Embryonic Stem Cells in Culture". *Bio/Technology.* Nov. 1989, vol. 7, pp. 1157-1161.
Pease et al. "Formation of Grem-Line Chimeras from Embryonic Stem Cells Maintained with Recombinant Leukemia Inhibitory Factor". *Experimental Cell Research.* 1990, vol. 190, pp. 209-211.
Gutierrez-Ramos et al. "In Vitro Differentation of Embryonic Stem Cells into Lymphcyte Precursors able to Generate T and B Lymphocytes in Vitro". *Immunology.* Oct. 1992, vol. 89, pp. 9171-9175.
Rathjen et al. "Properties and uses of Embryonic Stem Cells: Prospects for Application to Human Biology and Gene Therapy". *Reprod. Fertil. Dev..* 1998, vol. 10, pp. 31-47.
Bagutti et al. "Differentiation of Embryonal Stem Cells into Keratinocytes: Comparison of Wild-Type and $\beta_1$ Integrin-Deficient Cells". *Developmental Biology.* 1996, vol. 179, pp. 184-196.
Mountford et al. "Dicistronic Targeting Constructs: Reporters and Modifiers of Mammalian Gene Expression". *Developmental Biology.* May 1994, vol. 91, pp. 4303-4307.
Langhofer et al. "The Matrix Secreted by 804G Cells Contains Laminin-Related Components that Participate in Hemidesmosome Assembly in Vitro". *Journal of Cell Science.* 1993, vol. 105, pp. 753-764.
Sonnenberg et al. "Formation of Hemidesmosomes in Cells of a Transformed Murine Mammary Tumor Cell Line and Mechanisms involved in asherence of these Cells to Laminin and Kalinin". *Journal of Cell Science.* 1993, vol. 106, pp. 1083-1102.

(Continued)

*Primary Examiner*—Leon B Lankford
(74) *Attorney, Agent, or Firm*—Merchant & Gould P.C.

(57) ABSTRACT

The present invention relates to a method for inducing the differentiation of mammals' embryonic stem cells into keratinocytes, comprising the following steps of:
  isolating an extracellular matrix secreted by at least one mammals' cell type,
  cultivating mammals' embryonic stem cells in parallel in an undifferentiated condition in an appropriate culture medium in the presence of LIF,
  seeding the embryonic stem cells as a monolayer on said extracellular matrix,
  cultivating the thus seeded embryonic stem cells in the absence of LIF for a period of time sufficient for their differentiation into keratinocytes, and
  collecting the thus obtained keratinocytes.

10 Claims, No Drawings

OTHER PUBLICATIONS

Miquel et al. "Establishment and Characterization of Cell Line LSV5 That Retains the Altered Adhesive Properties of Human Junctional Epidermolysis Bullosa Keratinocytes". *Experimental Cell Research*. 1996, vol. 224, pp. 279-290.

Riddelle et al. "Formation of Hemidesmosomes in Vitro by a Transformed Rat Bladder Cell Line". *The Journal of Cell Biology*. 1991, vol. 112, pp. 159-168.

Boukamp et al. "Normal Keratinization in a Spontaneously Immortalized Aneupoid Human Keratinocyte Cell Line". *The Journal of Cell Biology*. 1988, vol. 106, pp. 761-771.

Procacci et al. "Differentiation of Embryonic Stem Cells into Keratinocytes". *Journal of Investigate Dermatology*. (Abstracts) 2000, vol. 115, pp. 518.

Bell et al. "Production of a Tissue-like Structure by Contraction of Collagen Lattices by Human Fibroblasts of Different Proliferative Potential in Vitro". *Cell Biology*. Mar. 1979, vol. 76, No. 3, pp. 1274-1278.

Bell et al. "The Reconstruction of Living Skin". *Supplement*. Jul. 1983, vol. 81, pp. 2s-10s.

Burke et al. "Successful Use of a Physiologically Accepteble Artificial Skin in the Treatment of Extensive Burn Injury". *Ann. Surg.*. Oct. 1981, vol. 194, No. 4, pp. 413-428.

Hansbrough et al. "Burn Wound Closure with Cultured Autologous Keratinocytes and Fibroblasts Attached to a Collagen-Glycosaminoglycan Substrate". *JAMA*. Oct. 20, 1989, vol. 262, No. 15, 2125-30.

Compton et al. "Skin Regenerated from Cultured Epithelial Autografts on Full-Thickness Burn Wounds from 6 Days to 5 years after Grafting". *Laboratory Investigation*. 1989, vol. 60, No. 5, 600-612.

Wilson et al. "Concentration-dependent Patterning of the Xenopus Ectoderm by BMP4 its Signal Transducer Smadl". *Development*. 1997, vol. 124, pp. 3177-3184.

Chang et al. "A Xenopus type 1 Activin Receptor Mediates Mesodermal but not Neural Specification During Embryogenesis". *Develpoment*. 1997, vol. 24, pp. 827-837.

Basset-Seguin et al. "Reconstructed Skin in Culture: a Simple Method with Optimal Differentiation". *Differentiation*. 1990, vol. 44, pp. 232-238.

Bagutti et al. "Dermal fibroblast-derived growth factors restore the ability of beta-1 integrin-deficient embryonic stem cells to differentiate into keratinocytes". *Developmental Biology*, vol. 231, No. 2, pp. 321-333 (2001).

Bagutti et al. "Differentiation of embryonic stem cells into keratinocytes: Comparison of wild-type and beta-1 integrin-deficient cells". *Developmental Biology*, vol. 179, No. 1, pp. 184-196 (1996).

Macinnes et al. "Differentiation and enrichment of functional keratinocytes from mouse embryonic stem (ES) cells". *Molecular Biology of the Cell*, vol. 11, No. Supplement, pp. 410A, (2000).

Schuldiner et al. "Effects of eight growth factors on the differentiation of cells derived from human embryonic stem cells". *Proceedings of the National Academy of Sciences of the United States*, vol. 97, No. 21, pp. 11307-11312 (2000).

Kramer et al. "Embryonic stem cell-derived chondrogenic differentiation in vitro: activation by BMP-2 and BMP-4". *Mechanisms of Development*, vol. 92, No. 2, pp. 193-205 (2000).

Nakayama et al. "Vascular endothelial growth factor synergistically enhances bone morphogenetic protein-4-dependent lymphohematopoietic cell generation from embryonic stem cells in vitro". *Blood*, vol. 95, No. 7, pp. 2275-2283 (2000).

Boyce et al. "Vitamin C regulates keratinocyte viability epidermal barrier and reduces wound contraction after grafting of cultured skin substitutes". *Journal of Investigative Dermatology*, vol. 118, No. 4, pp. 565-572 (2002).

Aberdam et al. "BMP-4 can induce keratinocyte commitment by inhibition of the neural antipoptosis pathway". *Journal of Investigative Dermatology*, vol. 119, No. 1, pp. 281 (2002).

Asselineau et al. "Co-operation action of vitamin C and epidermal keratinocytes in normal deposition of extracellular matrix and basement membrane components, in reconstructed skin". *Journal of Investigative Dermatology*, vol. 119, No. 1, pp. 259 (2002).

\* cited by examiner

KERATINOCYTES OBTAINED FROM EMBRYONIC STEM CELLS OF MAMMALS

OBJECT OF THE INVENTION

The present invention relates to a method for obtaining keratinocytes from mammals' embryonic stem cells.

A possible therapeutic application of such a method is the regeneration of tissues derived from keratinocytes, more particularly, the production of artificial skin.

STATE OF THE ART

The name "extracellular matrix" or "ECM" is the name generally given to the complex network of extracellular macromolecules which is in contact with most of the cells of pluricellular organisms.

The composition of the extracellular matrix and the form thereof vary depending on the tissue, so that it is more commonly referred to as extracellular matrices than as the extracellular matrix. However, extracellular matrices share in common their being made up of macromolecules which are essentially locally secreted proteins and polysaccharides being organized so as to form a three-dimensional network at the intercellular spaces level of most tissues.

Such macromolecules may include for example proteoglycans, fibrous proteins with an essentially structural function such as elastin and collagen, and fibrous proteins with an essentially adhesion function such as fibronectin and laminins.

The extracellular matrix is not only a biological "glue", but it also forms highly dedicated structures such as cartilage, tendons, lamina basement membrane, skeleton and teeth.

Additionally, it has been found that extracellular matrices play a critical part in regulating the behaviour of cells they are in contact with. They are thus involved in as different phenomena as cellular development, proliferation, metabolism, shape and polarity of the cells. Another phenomenon where extracellular matrices are involved is the cell differentiation.

Embryonic stem cells are derived from embryonic totipotent cells. These are pluripotent cells capable to differentiate in vivo into any cellular type (Bradley et al., Nature 309, 255–256 (1984); Nagy et al., Development 110, 815–821 (1990)) and in vitro into a more limited number of cellular types (Doetschman et al., J. Embryol. Exp. Morph. 87, 27–45 (1985); Wobus et al., Biomed. Biochim. Acta 47, 965–973 (1988); Robbins et al., J. Biol. Chem. 265, 11905–11909 (1990); Schmitt et al., Genes and Development 5, 728–740 (1991)).

However, the embryonic stem cells are difficult to culture in a laboratory and their culture requires the addition in the culture medium of a differentiation inhibiting factor, commonly referred to as "LIF" (Leukemia Inhibiting Factor), so as to avoid any spontaneous differentiation phenomenon (Williams et al., Nature 336, 684–687 (1988); Smith et al., Nature 336, 688–690 (1988); Gearing et al., Biotechnology 7, 1157–1161 (1989)).

The LIF is a secretion protein able to be provided by maintaining embryonic stem cells on a nutrient layer of cells producing such a LIF (E. J. Robertson, Teratocarcinomas and Embryonic stem cells: a practical approach, Washington D.C., IRL Press (1987)) or, in the absence of a nutrient layer, by adding purified LIF to the culture medium (Pease et al., Exp. Cell. Res. 190, 209–211 (1990)).

It has been demonstrated that the spontaneous differentiation of embryonic stem cells occurs as soon as the LIF is removed from the culture medium where the cells are present, and that it could also be induced through manipulation under certain conditions (Gutierrez-Ramos et al., Proc. Nat. Acad. Sci. 89, 9111–9175 (1992)).

Such a differentiation occurs under the effect of the embryonic stem cells aggregation, causing embryoid bodies (three-dimensional structures) to be formed, from which cells differentiate from each other into various cellular types.

Rudnicki et al. disclosed a general method for inducing a differentiation of embryonic stem cells, the so-called "hanging drop method" (Rudnicki et al., <<Cell culture methods and induction of differentiation of embryonal carcinoma cell lines>>, in *Teratocarcinomas and embryonic stem cells: a practical approach*, (E. J. Robertson, op. cit.), 19–49 (1987), IRL Press, Oxford). In such a method, so that the embryonic stem cells differentiate from each other, it is required to form three-dimensional structures referred to as "embryoid bodies" such as hereinabove mentioned.

The absence of LIF in such a method is required for allowing the embryonic stem cells to be differentiated from each other. After 3 days, the formed embryoid bodies are transferred onto bacteriological Petri dishes and are kept suspended for 2 days, so as to avoid their adhesion and to enhance their growth. The embryoid bodies are then allowed to adhere on cellular culture dishes. As early as the second day after adhesion, various cellular types are to be observed within those bodies, amongst others, beating cells (cardiomyocytes). Depending on the culture conditions being used, skeletal and smooth muscle cells, nerve cells, glial cells and hematopoietic system derivatives are identified (Rathjen et al., <<Properties and uses of embryonic stem cells: prospects for application to human biology and gene therapy>>, Reprod. Fertil. Dev. 10(1), 31–47 (1998), Review).

Recently, culture conditions allowing to induce in a predominant and reproducible way the differentiation of embryonic stem cells towards a particular lineage have been developed (Rathjen et al., op. cit.).

It is from now on clearly observed that the LIF holds the pluripotent embryonic stem cells under a undifferentiated form, and that the removal thereof from the cellular medium allows such cells to initiate, under the form of embryoid bodies, a differentiation programme.

The document by Bagutti et al. (Bagutti et al., Developmental Biology 179, 184–196 (1996)) more particularly discloses the spontaneous differentiation of mouse embryonic stem cells into keratinocytes using the hanging drop method, the keratinocytes appearing as from the 21$^{st}$ day.

However, there is currently not yet a method for inducing the differentiation of the embryonic stem cells into keratinocytes which would be a true alternative, in terms of speed and yield, to the hanging drop method.

AIMS OF THE INVENTION

The aim of the present invention is to provide a method and means for inducing the differentiation of embryonic stem cells into keratinocytes, allowing to more quickly obtain more differentiated keratinocytes, compared to the state of the art methods.

Another aim of this invention is also to provide a method and means for inducing the differentiation of mammal's embryonic stem cells into keratinocytes which would be reproducible and reliable.

SUMMARY OF THE INVENTION

The present invention relates to obtaining keratinocytes from mammals' embryonic stem cells, in particular to a method for inducing the differentiation of mammals' embryonic stem cells into keratinocytes, comprising the following steps of:

isolating an extracellular matrix secreted by at least one mammals' cell type, cultivating mammals' embryonic stem cells in parallel in an undifferentiated condition in an appropriate culture medium, seeding then said embryonic stem cells as a monolayer on said extracellular matrix or on one or more fractions thereof comprising particular components, including laminin-5, type IV collagen, type I collagen or fibronectins, cultivating then said thus seeded embryonic stem cells in the absence of the above-mentioned LIF for a period of time sufficient for obtaining a differentiation into keratinocytes, and collecting the thus obtained keratinocytes, isolating and amplifying them using known cloning techniques (dispase, trypsin, cell sorting).

Advantageously, the embryonic stem cells are previously held in an undifferentiated condition in the presence of the LIF, preferably at a concentration in the order of $10^3$ units/ml of culture.

According to the invention, inducing the differentiation of embryonic stem cells on an extracellular matrix is initiated as early as the $8^{th}$ day and is widely progressing after 15 days. This time factor is in no way limiting and could be accelerated using various methods able to be adjusted by the man of the art.

Additionally, it is also possible to treat the embryonic strains before differentiation into keratinocytes through various genetic modifications, in particular, through genetic modifications on genes of the major histocompatibility complex (MHC), so as to create universal immunotolerant pluripotent lineages.

Most advantageously, the embryonic stem cells being seeded on the extracellular matrix are cultivated in the presence of BMP-4 and ascorbic acid.

Another aspect of the present invention relates to the production of artificial skin, more particularly, an epidermis tissue comprising said thus obtained keratinocytes, as well as their use for treating patients suffering from thermal wounds (more particularly, severely burnt people), vascular wounds (such as ulcers), or patients suffering from pathologies associated to healing deficiencies.

The present invention will be further detailed using the description of a preferred embodiment of the invention presented by way of non-limiting illustration of the object of the invention.

DETAILED DESCRIPTION OF THE INVENTION

The hereunder presented examples illustrate the method according to this invention. In those examples, a CGR8 murine embryonic stem cell lineage (Mountford et al., Proc. Natl. Acad. Sci. USA 91, 4303–4307 (1994)), at the blastocyste stage, has been cultivated in an undifferentiated condition in the presence of LIF (Leukemia Inhibiting Factor) ($10^3$ units/ml) on previously gelatinized culture dishes (0.1% in PBS) under humid atmosphere at 37° C. and under 5% $CO^2$ in an incubator.

The culture medium consists in GMEM/BHK21 (Glasgow's Modified Eagles's Medium—GIBCO BRL) supplemented with 10% foetal calf serum (FCS; Hyclone), 0.23% sodium bicarbonate, 1% non essential amino acids, 2 mM glutamine, 1 mM sodium pyruvate and 0.1 mM β-mercaptoethanol.

These embryonic stem cells in an undifferentiated condition are then seeded, in the absence of LIF, either on an amorphous substrate (glass or plastic material, negative control), or on gelatine, either on coated laminas of extracellular matrix from various cell types (see hereunder). Cells from epithelial origin have thereby been tested (804G lineage; Rac-11P lineage; SCC25 lineage; MCF-10 A lineage; KHSV lineage; $NBT_{II}$ lineage; HaCaT lineage) as well as fibroblastic cells (J2 lineage; NIH-3T3 lineage); human dermis fibroblasts in a primary culture). The epithelial lineages produce, amongst others, high laminin-5 amounts, and form in vitro numerous anchorage structures of the hemidesmosome type (Langhofer M. et al., J. Cell Science 105, 753–764 (1993)).

The embryonic stem cells have also been seeded on coated laminas only with major components of the basal laminas (purified laminin-5; collagen of the purified type IV; collagen of the purified type I; purified fibronectins).

In order to collect their extracellular matrix, the above-mentioned lineages have been cultivated at confluence on the lamellas. Once confluence has been reached, those cells are removed using a solution consisting in PBS containing 20 mM ammonium hydroxide or a HBSS (Hanks balanced salt solution, GIBCO-BRL) solution containing 20 mM EDTA, 20 mM Hepes and 1 mM EGTA) so as to only keep the extracellular matrix intact on the lamellas. The thus "coated" lamellas have been stored at 4° C.

The presence of keratinocytes has been evaluated through immunofluorescent approach with mouse monoclonal antibodies raised against the 14 (K14; Sigma) and 5 (Dr. B. Lane, Dundee University, UK) cytokeratins. The 14 and 5 cytokeratins are part of intermediary filaments specific to the basal keratinocytes. The embryonic stem cells were cultivated on sterile glass lamellas with or without extracellular matrix being deposited. After being washed with PBS, the cells were fixed using cold methanol for 10 minutes at –20° C. The cells were then washed with PBS before being incubated for one hour with the anti-K14 primary antibody ($1/100^{th}$ diluted in a PBS buffer containing 3 mg/ml BSA, in a humid chamber) or with the anti-K5 primary antibody ($1/5^{th}$ diluted in the same buffer, in a humid chamber). After being again washed with PBS for 5 minutes, the lamellas were incubated for one hour in the dark with a relevant secondary antibody coupled to a marker. After a final rinsing operation, the lamellas were incubated with a nuclear marker (Hoechst or propidium iodide), $1/1000^{th}$ diluted for 10 minutes away from light, and then mounted on laminas after being washed with distilled water. All operations were performed at room temperature. The laminas were observed under a "Zeiss Axiophot" microscope.

The obtained results showed that, on an amorphous support, despite a spontaneous and anarchic differentiation, the cells did not differentiate into keratinocytes, even after a 15 day culture without LIF. The results on gelatine showed that only a tiny portion of CGR8 embryonic stem cells were differentiated into keratinocytes: a keratinocyte sporadic presence could be observed after 8 days of culture and such a proportion is increased at the $15^{th}$ day, the observed keratinocytes staying predominantly isolated, without forming clusters.

The results obtained on coated laminas with a total or partial fraction of the extracellular matrix of the cellular types were found to be drastically different from the results obtained on an amorphous support.

Results Obtained on the Extracellular Matrix Originating from the Various Cellular Types being Used A keratinocyte differentiation has been obtained on the various extracellular matrices being investigated. However, the induction efficiency variations between those various matrices require to distribute them into two distinct categories: (A) matrices with a high induction capacity; (B) matrices with an average induction capacity (also see table I).

(A) Matrices with a High Induction Capacity of the Keratinocyte Differentiation a) Extracellular matrix produced by NHF cells: the NHF (normal human fibroblasts) were obtained from prepuce biopsies and maintained in DMEM (Dulbecco's Modified Eagles's Medium—GIBCO BRL) supplemented with 10% SVF (Hyclone). The cells were maintained in a humid atmosphere at 37° C. and under 5% $CO^2$ in an incubator. At confluence, the NHF cells were removed and the CGR8 embryonic stem cells were seeded on the extracellular matrix deposited by the NHF cells.

On the 8th day of culture of the CGR8 embryonic stem cells on the matrix produced by the NHFs, numerous isolated keratinocytes could be identified through immunofluorescence. On the fifteenth day, more numerous keratinocytes could be observed in big clusters ("patches") forming some kind of an epidermal small sheet. Numerous isolated keratinocytes can also be detected.

Thus, the presence of a matrix secreted by the NHF cells causes a significant effect on the differentiation of the embryonic stem cells into keratinocytes. Indeed, whereas no differentiation could be observed in a direct culture on an amorphous substrate even after a 15-day culture, a large amount of keratinocytes is obtained in a direct culture on the extracellular matrix produced by the NHF cells. Moreover, such a differentiation is earlier than that obtained via the embryoid bodies since as early as the $8^{th}$ day of culture in a monolayer without LIF, a high proportion of keratinocytes is to be observed.

b) Extracellular matrix produced by the NIH-3T3, Rac-11P, KHSV and $NBT_{II}$ cellular lineages:

the above-mentioned experiment (NHF cells) was reproduced on the matrix produced by the following cellular lineages:

i) NIH-3T3: ATCC, CRL 1658. Such cells were maintained in DMEM (Dulbecco's Modified Eagles's Medium—GIBCO BRL) supplemented with 10% SVF (Hyclone). The cells were maintained in a humid atmosphere at 37° C. and under 5% $CO^2$ in an incubator.

ii) Rac-11P: Sonnenberg A. et al. (1996) J. Cell Science 106:1083. Such cells were maintained in DMEM (Dulbecco's Modified Eagles's Medium—GIBCO BRL) supplemented with 10% SVF (Hyclone). The cells were maintained in a humid atmosphere at 37° C. and under 5% $CO^2$ in an incubator.

iii) KHSV: Miquel C. et al. (1996). Exp. Cell Res. 224: 279–290. Such cells were maintained in DMEM (Dulbecco's Modified Eagles's Medium—GIBCO BRL) containing 50% Ham F12 medium (GIBCO BRL) and supplemented with 10% SVF (Hyclone), 0.4 µg/ml hydrocortisone, 0.1 ng/ml cholera toxin and 10 ng/ml Epidermal Growth factor. The cells were maintained in a humid atmosphere at 37° C. and under 5% $CO^2$ in an incubator.

iiii) $NBT_{II}$: ATCC, CRL 1655. Such cells were maintained in DMEM (Dulbecco's Modified Eagles's Medium—GIBCO BRL) supplemented with 10% SVF (Hyclone). The cells were maintained in a humid atmosphere at 37° C. and under 5% $CO^2$ in an incubator.

In these four other examples, similar results are obtained to those obtained with the NHF cell matrix. Indeed, the deposit of the embryonic stem cells on the coated laminas with the extracellular matrix produced by such cellular lineages leads to the appearance of K14-positive keratinocytes as early as the $8^{th}$ day of culture in a monolayer. The qualitative and quantitative differences are shown in table 1.

(B) Matrices with an Average Induction Capacity of the Keratinocyte Differentiation a) Extracellular matrix produced by the 804G lineage: the 804G lineage, derived from epithelial cells of rat's bladder (Riddelle K S et al., J. (1991) J. Cell Biol. 112, 159–168), has been previously cultivated in DMEM (Dulbecco's Modified Eagles's Medium—GIBCO BRL) supplemented with 10% SVF (Hyclone). The cells were maintained in a humid atmosphere at 37° C. and under 5% $CO^2$ in an incubator. At confluence, the 804G cells were removed and the CGR8 embryonic stem cells were seeded on the extracellular matrix deposited by the 804G cells.

On the 8th day of culture of the CGR8 embryonic stem cells on the matrix produced by the 804Gs, isolated keratinocytes could be identified through immunofluorescence. On the fifteenth day, more keratinocytes could also be detected.

Thus, the presence of a matrix secreted by the 804G cells causes a significant effect on the differentiation of the embryonic stem cells into keratinocytes. Indeed, whereas no differentiation could be observed in a direct culture on an amorphous substrate even after a 15-day culture, a large amount of keratinocytes is obtained in a direct culture on the extracellular matrix produced by the 804G cells. Moreover, such a differentiation is earlier than that obtained via the embryoid bodies since as early as the $8^{th}$ day of culture in a monolayer without LIF, a high proportion of keratinocytes is to be observed. The qualitative and quantitative differences are shown in table 1.

b) Extracellular matrix produced by the SCC25, MCF-10A and HaCaT cellular lineages:

the above-mentioned experiment (804G cells) was reproduced on the matrix produced by the following cellular lineages:

i) SCC25: ATCC CRL 1628. Such cells were maintained in DMEM (Dulbecco's Modified Eagles's Medium—GIBCO BRL) containing 50% Ham F12 medium (GIBCO BRL) and supplemented with 10% SVF (Hyclone) and 0.4 µg/ml hydrocortisone. The cells were maintained in a humid atmosphere at 37° C. and under 5% $CO^2$ in an incubator.

ii) MCF-10A: ATCC CRL 10317. Such cells were maintained in DMEM (Dulbecco's Modified Eagles's Medium—GIBCO BRL) containing 25% Ham F12 medium (GIBCO BRL) and supplemented with 10% SVF (Hyclone), 1.5 ng/ml triiodo-L-thyronin, 5 µg/ml insulin, 0.5 µg/ml hydrocortisone, 20 µg/ml adenine, 5 µg/ml apotransferrin and 2 ng/ml Epidermal Growth Factor. The cells were maintained in a humid atmosphere at 37° C. and under 5% $CO^2$ in an incubator.

iii) HaCaT: Boukamp P. et al. (1988). J. Cell Biol. 106: 761–771. Such cells were maintained in DMEM (Dulbecco's Modified Eagles's Medium—GIBCO BRL) containing 50% Ham F12 medium (GIBCO BRL) supplemented with 10% SVF (Hyclone) and 1% of a non essential amino acid solution. The cells were maintained in a humid atmosphere at 37° C. and under 5% $CO^2$ in an incubator.

In these three other examples, similar results are obtained to those obtained with the 804G cell matrix. Indeed, the deposit of the embryonic stem cells on the coated laminas with the extracellular matrix produced by such cellular lineages leads to the appearance of K14-positive keratinocytes as early as the $8^{th}$ day of culture in a monolayer. The qualitative and quantitative differences are shown in table 1.

Results Obtained with the D3 Embryonic Stem Cell Lineage on the Extracellular Matrix Produced by the Above-Mentioned Lineages The D3 lineage (Doetschman et al., J. Embryol. Exp. Morphol. 87, 27–45 (1985)) was previously cultivated on a nutrient layer of murine embryonic fibroblasts.

Results similar to those obtained with the lineage of CGR8 embryonic stem cells have been obtained.

Results similar to those obtained with the matrices were observed using the conditioned medium of the same cellular lineages.

The method according to the present invention has therefore the advantage, compared to the hanging drop method as applied by Bagutti et al. (op. cit.) for inducing the differentiation of mouse embryonic stem cells into keratinocytes, of allowing keratinocytes to be more efficiently and more quickly obtained.

This is particularly important in cases where it is required to mass produce such keratinocytes, as for example in the case of producing artificial skin. The skin is indeed an organ consisting in three tissues from different embryological origins: the ectoderm for the epidermis, the mesoderm for the dermis and the hypodermis. The keratinocytes account for 95% of the epidermal population and they permanently renew from a basal germinal layer following a differentiation programme ending to the formation of a stratum corneum consisting of corneocytes.

The production of artificial skin is a technology aiming at treating patients suffering from thermal wounds, more particularly severely burnt people, vascular wounds such as ulcers, as well as patients suffering from pathologies associated to healing deficiencies.

Three main pattern types for regenerating human skin in laboratory are currently available and implementable: the equivalent dermis (Procacci et al., J. Inv. Dermatol. 115, 518 (2000); Bell et al., Proc. Natl. Acad. Sci. USA 76, 1274–1278 (1979); Bell et al., J. Invest. Dermatol. 81, 2s–10s (1983)), the allogenic dermo-epidermal composite skin (Burke et al., Am. Surg. 194, 413–428 (1981)) and the allogenic culture epidermis (Hansbrough et al., J. Am. Med. Ass. 262, 2125–2140). Such different patterns are prepared from primary cultures of keratinocytes and/or fibroblasts.

Whereas such patterns are well suited for pharmaceutical studies, their use for therapeutic purposes is however considered unsatisfactory for a number of surgical teams over the world, more particularly as it is associated with graft rejection (Compron et al., Lab. Invest. 60, 600–612 (1989)).

The autograft of regenerated epidermis from a cutaneous biopsy on the patient, followed by a culture of the keratinocytes for about three weeks would be the best solution as it would prevent any immunological rejection risk. However, such a solution has the disadvantage of being long to implement.

Currently, for the surgeon, the expanded allograft of corpse skin remains the best cutaneous substitute. However, this solution is not feasible in the long term because, in addition to the problem of the lack of donors, such a solution exposes the patient to a potential viral contamination.

That is why attempts have been made for providing an alternative to such methods.

Since the culture of human embryonic stem cells is from now on possible in a laboratory, the represented methods allow for the unlimited achievement of graftable regenerated epidermis without rejection risk, the embryonic stem cells having the double advantage of being "immortal" without being immortalized and of being easy to handle through transfection and homologous recombination. In order that such keratinocytes remain in the recipient patient, modifications of some loci, such as that of the genes of the major histocompatibility complex playing a part in the recognition of foreign cells by the immune system, allow to create universal immunotolerant totipotent lineages.

| Effect of various matrices on the keratinocyte differentiation | | |
|---|---|---|
| Matrices | D8 | D15 |
| Glass | − | − |
| Gelatine | −/+ | + |
| NHF | +++ | ++++ |
| 3T3 | +++ | ++++ |
| 804G | ++ | ++ |
| Racll P | ++ | ++++ |
| SCC25 | ++ | + |
| MCF10 | +++ | + |
| KHSV | +++ | +++ |
| NBTII | + | +++ |
| HaCaT | + | + |

The ES cells were deposited on matrices secreted by cells from various origins. The presence of newly formed keratinocytes was detected on 8 (D8) and 15 days (D15) through anti-keratin 14 immunomarking.

The presence of K14-positive cells is quantitatively represented by:

(−) an absence of keratinocytes; (+) a low amount of keratinocytes;

average (++), high (+++) and very high (++++) amounts of keratinocytes.

Such a quantification represents the results of various independent experiments performed in triplicate.

Effect on the Differentiation of Additives in the Culture Medium

It has been experimentally observed that the embryonic stem cells (ES cells) could be induced to differentiate from one another in keratinocytes through the addition of BMP-4 in the culture medium, whatever the substrate on which the cells are cultivated.

BMP-4 is a morphogenic protein belonging to the TGF-β superfamily. It is known that the neuroectodermal cells, during the early embryonic development, become either epidermal or neuronal, depending on the BMP-4 local concentration, the high concentration of BMP-4 enhancing the formation of the epidermis (Wilson P. et al. (1997) *Development* 124, 3177–3184; Chang C. et al. (1997) *Development* 124, 827–837).

According to the method of the invention, as soon as the LIF factor has been removed, a 0,5 nM BMP-4 solution diluted in 0,1% PBS-BSA was added to the culture medium with which the embryonic stem cells are cultivated in a monolayer, and this treatment was repeated every 2 days. It was possible to observe, through immunomarking with a anti-cytokeratin-14 antibody, the appearance of an important proportion of keratinocytes on the 15$^{th}$ day of treatment.

It was also observed that if, instead of adding to the culture medium a BMP-4 solution, a solution was added in the same conditions containing 50 µg/ml ascorbic acid, an important proportion of keratinocytes on the 15$^{th}$ day of treatment appeared.

In addition, the deposition in the absence of LIF of undifferentiated stem cells, cultivated on an equivalent or de-epidermized dermis, allows for the formation of a double layer of keratinocyte differentiated cells as early as the 8$^{th}$ day of immersion culture. Through immunofluorescence, all the cells adhering to the dermal substrate indeed proved to be positive for the cytokeratin-14. At the end of fourteen additional days of cell culture at the air-liquid interface according to the method disclosed by Basset-Seguin N. et al. (Basset-Seguin N. et al. (1990) Differentiation 44, 232–238), it is possible to obtain a stratified epidermis having all the markers specific for the various murine epidermis cell layers, as well as the deposit by the laminin-5 basal layer at the level of the basal lamina.

Comparatively, adding BMP-4 in the culture medium of embryonic stem cells, already upon the deposit on the equivalent dermis, allows to obtain a double layer of keratinocyte differentiated cells as early as the 4$^{th}$ day of immersion culture.

The invention claimed is:

1. A method for inducing the differentiation of mammalian embryonic stem cells into keratinocytes, comprising the following steps of:
   isolating an extracellular matrix secreted by at least one mammals' cell type, and coating the extracellular matrix on a solid support,
   seeding undifferentiated embryonic stem cells as a monolayer on said extracellular matrix,
   cultivating the thus seeded embryonic stem cells in the absence of LIF for a period of time sufficient for their differentiation into keratinocytes, and
   collecting the thus obtained keratinocytes.

2. A method according to claim 1 wherein the culture period of the embryonic stem cells seeded on the extracellular matrix is efficient as early as the 8$^{th}$ day and lower than 21 days.

3. A method according to claim 1, wherein the embryonic stem cells seeded on the extracellular matrix are cultivated in the presence of BMP-4 or ascorbic acid.

4. A method according to claim 1, wherein the cells having their extracellular matrix collected are human cells, except for germ cells.

5. A method for producing an artificial skin from mammalian embryonic stem cells comprising the following steps of:
   inducing the differentiation of said embryonic stem cells into keratinocytes using the method according to claim 1; and
   continuing the culture of the differentiated cells at the air-liquid interface for a time sufficient for obtaining the formation of a stratified artificial epidermis.

6. The method of claim 1 comprising cultivating mammalian embryonic stem cells in an undifferentiated condition in an appropriate culture medium in the presence of LIF prior to seeding.

7. A method according to claim 6, wherein the embryonic stem cells are previously maintained in an undifferentiated condition using the LIF factor at a concentration in the order of $10^3$ units/ml of culture.

8. The method of claim 1, wherein the extracellular matrix comprises one or more of laminin-5, type IV collage, type I collagen or fibronectins.

9. The method of claim 1, wherein in the extracellular matrix is isolated from mammalian fibroblastic or epithelial cells.

10. The method of claim 1, wherein isolating and coating the extracellular matrix comprises:
    cultivating the mammalian cells at confluence on a solid support; and
    removing the mammalian cells from the support leaving the extracellular matrix coated on the solid support.

* * * * *